(12) United States Patent
Copeland

(10) Patent No.: US 10,145,777 B1
(45) Date of Patent: Dec. 4, 2018

(54) REMOTE AEROSOL INJECTION SYSTEMS AND METHODS FOR USE

(71) Applicant: Wayne A. Copeland, Ontario (CA)

(72) Inventor: Wayne A. Copeland, Ontario (CA)

( * ) Notice: Subject to any disclaimer, the term of this patent is extended or adjusted under 35 U.S.C. 154(b) by 175 days.

(21) Appl. No.: 14/988,717

(22) Filed: Jan. 5, 2016

Related U.S. Application Data

(60) Provisional application No. 62/100,021, filed on Jan. 5, 2015.

(51) Int. Cl.
*G01N 15/08* (2006.01)
*B01D 46/42* (2006.01)
*F24F 3/16* (2006.01)

(52) U.S. Cl.
CPC ............. *G01N 15/08* (2013.01); *B01D 46/42* (2013.01); *F24F 3/161* (2013.01); *B01D 2273/18* (2013.01); *F24F 2003/1614* (2013.01); *G01N 2015/084* (2013.01)

(58) Field of Classification Search
CPC .. G01N 15/08; G01N 2015/084; B01D 46/42; B01D 2273/18; F24F 3/161; F24F 2003/1614
USPC ............................................................ 73/38
See application file for complete search history.

(56) References Cited

U.S. PATENT DOCUMENTS

| | | | | |
|---|---|---|---|---|
| 6,110,259 A | * | 8/2000 | Schultz .................. | A61B 18/00 55/385.1 |
| 6,770,108 B2 | * | 8/2004 | Cherry, Sr. ............ | B01D 46/10 210/435 |
| 2006/0042359 A1 | * | 3/2006 | Morse ................. | G01M 3/3281 73/40 |
| 2006/0053864 A1 | * | 3/2006 | Morse ................ | B01D 46/0086 73/23.2 |
| 2006/0112757 A1 | * | 6/2006 | Morse ................ | B01D 46/0086 73/38 |
| 2006/0272301 A1 | * | 12/2006 | Morse ................ | B01D 46/0086 55/439 |
| 2006/0276120 A1 | * | 12/2006 | Cherry, Sr. ............. | F24F 13/28 454/56 |
| 2012/0104744 A1 | * | 5/2012 | Petty ..................... | F16L 33/222 285/31 |
| 2016/0175623 A1 | * | 6/2016 | Alexander ............... | A62B 7/14 434/262 |

* cited by examiner

*Primary Examiner* — Natalie Huls
*Assistant Examiner* — Monica S Young
(74) *Attorney, Agent, or Firm* — William A. English; Vista IP Law Group LLP

(57) ABSTRACT

Systems and methods are provided for testing filters. In an exemplary embodiment, a method is provided for testing a filter within a duct system that includes mounting a port to a wall of a duct of the system, positioning a section of tubing within the duct from the port until an outlet end of the tubing is disposed adjacent a filter, connecting a source of test media to the port; delivering test media from the source through the port and tubing into the duct to the filter, and scanning the filter for test media.

23 Claims, 6 Drawing Sheets

REMOTE AEROSOL INJECTION SYSTEMS AND METHODS FOR USE

RELATED APPLICATION DATA

This application claims benefit of provisional application Ser. No. 62/100,021, filed Jan. 5, 2015, the entire disclosure of which is expressly incorporated by reference herein.

FIELD OF THE INVENTION

The present invention relates to systems and methods for testing filters, and more particularly, to systems and methods for testing filters during required certification and/or other activities, e.g., in duct systems that either have no accessibility and/or do not allow feeding of the aerosol (smoke) through the system, e.g., I.E. systems with filtered and non-filtered areas, remote located cleanrooms, or HEPA filters.

BACKGROUND

With the onset of regulations such as USP 797 and USP 800, it can be challenging to test filter systems, e.g., during required certification activities, where accessibility is limited or an HVAC system does not allow feeding of the aerosol (smoke) through the system. This challenge now reaches from the big Pharmaceutical world to the everyday world of Compounding Pharmacies, and to small neighborhood pharmacies. Most of these small remote clean spaces add either terminal HEPA filters or in most cases Fan Filter Units since they are adding these filters into an existing system that does not have the capacity to accommodate the resistance of HEPA filtration. This is a problem that faces certification companies throughout the world.

SUMMARY

The present invention is directed to systems and methods for testing filters. More particularly, the present invention is directed to systems and methods for testing filters during required certification and/or other activities, e.g., in duct systems that either have no accessibility and/or do not allow feeding of the aerosol (smoke) through the system, e.g., I.E. systems with filtered and non-filtered areas, remote located cleanrooms, or HEPA filters.

In accordance with one embodiment, a method is provided for testing a filter within a facility that includes mounting an injection port to a wall or ceiling of an accessible location within the facility; positioning a section of tubing from the injection port until an outlet end of the tubing is disposed adjacent a filter; connecting a source of test media to the injection port; delivering test media from the source through the injection port and tubing into the duct to the filter; and scanning the filter for test media.

In accordance with another embodiment, a method is provided for installing a testing system for testing a filter of a duct system of a facility that includes mounting an injection port to a wall of an accessible location within the facility; coupling a first end of a section of tubing to the injection port; mounting a delivery port to a wall of a duct delivering air to the filter; and coupling a second end of the section of the tubing to the delivery port, thereby creating a path for test media from the accessible location to the filter.

In accordance with still another embodiment, a method is provided for installing a testing system for testing filters of a duct system of a facility that includes mounting a plurality of injection ports to a wall or ceiling of an accessible location within the facility; coupling a first end of respective sections of tubing to each injection port; mounting a delivery port to a wall of a duct delivering air to each filter; and coupling a second end of the respective sections of the tubing to respective delivery ports, thereby creating a path for test media from the accessible location to each of the filters.

In accordance with yet another embodiment, a method is provided for testing a filter of a duct system comprising an injection port mounted to a wall or ceiling of an accessible location within the facility and a section of tubing extending from the injection port to a delivery port in a duct adjacent a filter, the method including connecting a source of test media to the injection port; delivering test media from the source through the injection port and tubing into the duct to the filter; and scanning the filter for test media.

In accordance with another embodiment, a kit is provided for installing a testing system for testing a filter of a duct system of a facility that includes an injection port including a mounting plate and a fitting extending from mounting plate; an elbow comprising a first end configured to be coupled to the fitting and a second end including one or more barb connectors for connecting to a first end of a section of tubing; and a nipple comprising a first end configured to be coupled to a delivery port and a second end including one or more barb connectors for connecting to a second end of a section of tubing. Optionally, the kit may also include a delivery port including a mounting plate and a fitting and/or a section of tubing.

In accordance with still another embodiment, a system is provided for testing a filter of a duct system within a facility that includes an injection port mounted to a ceiling of an accessible location within the facility; a delivery port mounted to a wall of a duct delivering air to the filter; and a section of tubing including a first end coupled to the injection port and a second end of coupled to the delivery port, thereby creating a path for test media from the accessible location to the filter.

Other aspects and features including the need for and use of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments. The drawings illustrate exemplary embodiments, in which.

DETAILED DESCRIPTION OF THE EXEMPLARY EMBODIMENTS

Figure 1:
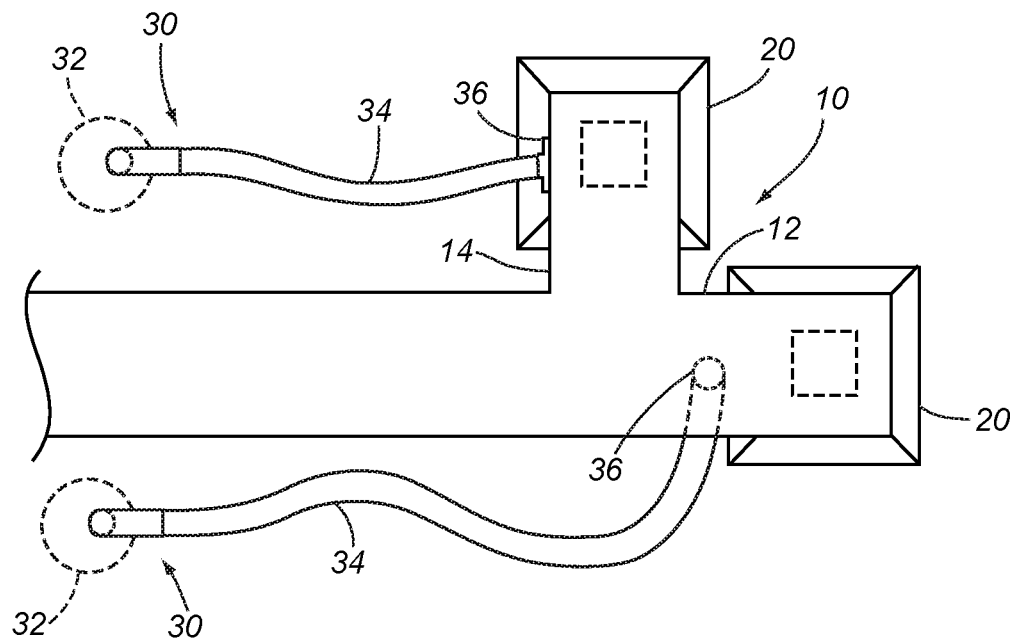
FIG. 1 is a schematic showing an exemplary embodiment of a portion of a duct system of a facility including first and second branches communicating with respective filters, and including port assemblies for delivering test materials to the filters from a location remote from the duct system.

Turning to the drawings, FIGS. 1A and 1B show an exemplary embodiment of a duct system 10 within a building or other facility (not shown) that includes a first branch 12 and a second branch 14 communicating with respective filters 20. As shown, port assemblies 30 are provided that communicate from test or injection ports 32 to the first and second branches 12, 14, thereby enabling aerosol or other test materials to be delivered to the filters 20 for testing, e.g., to meet certification activities and/or other requirements.

Figure 3A:
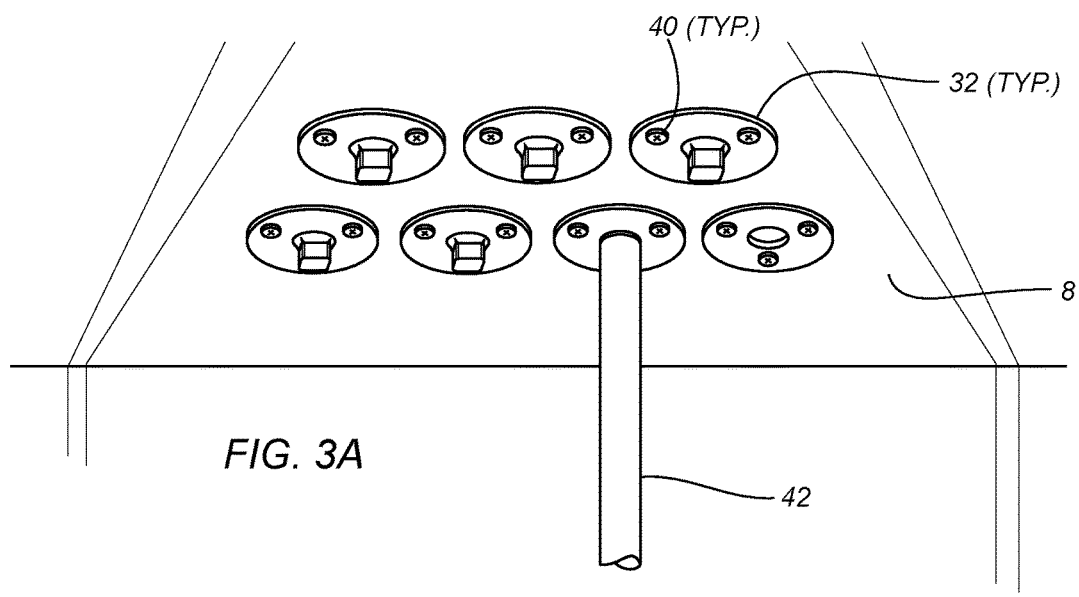
FIGS. 3A and 3B are details of exemplary installations of multiple injection ports for respective port assemblies mounted to a ceiling of a facility.
Figure 3B:
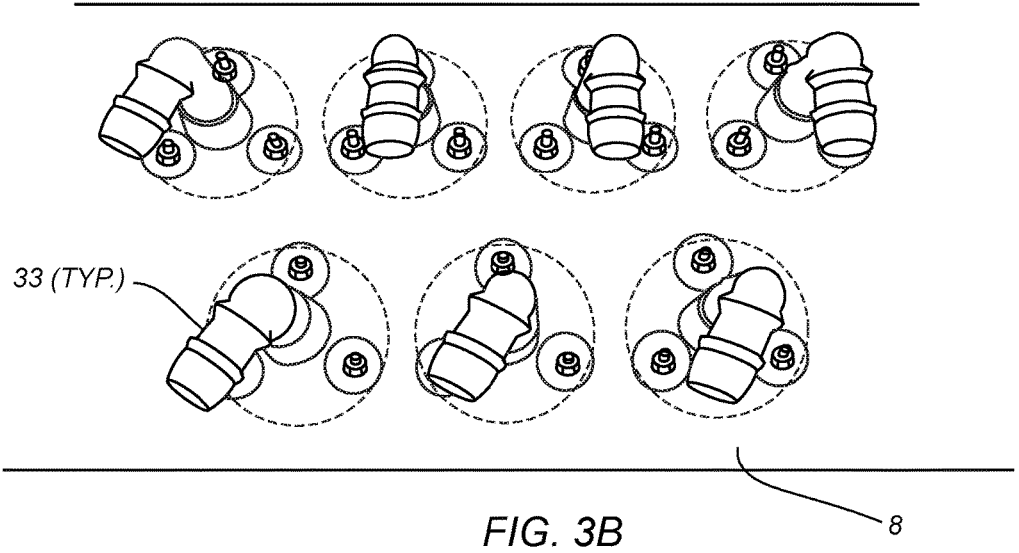

As best seen in FIG. 1B, in an exemplary configuration, a first port assembly 30 has been mounted to the system 10 that includes an injection port 32, e.g., mounted to a ceiling 8 or other location that is easily accessible within the facility, and a section of tubing 34 that extends from the injection port 32 to a plate or other connector 36 in the first branch 12. As shown in FIGS. 3A and 3B, the injection ports 32 may be mounted into a ceiling 8 or other panel within the facility, thereby providing ready access to the port assemblies 30 without having to access the duct system 10, attic space, and the like, as described elsewhere herein.

Figure 4A:
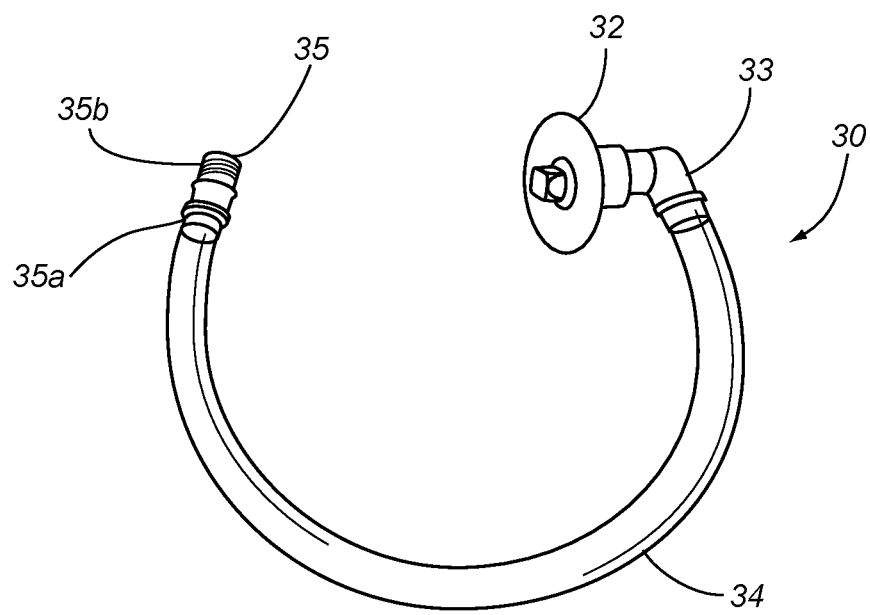
FIG. 4A is a side view of an exemplary embodiment of a port assembly.
Figure 4B:
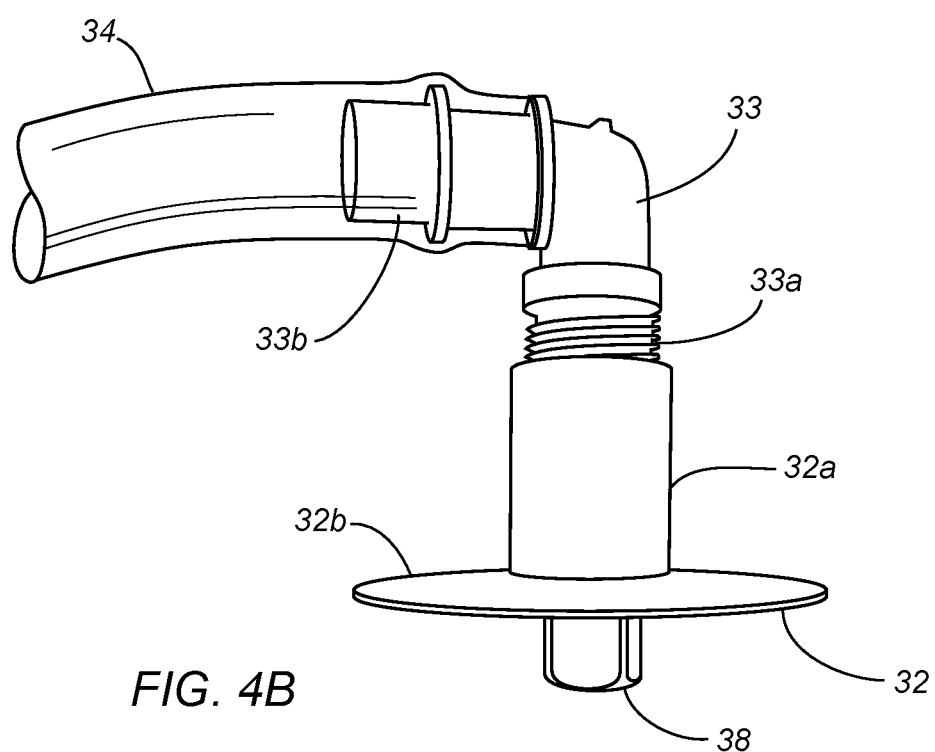
FIGS. 4B and 4C are side and end views of the port assembly of FIG. 4A.
Figure 4C:
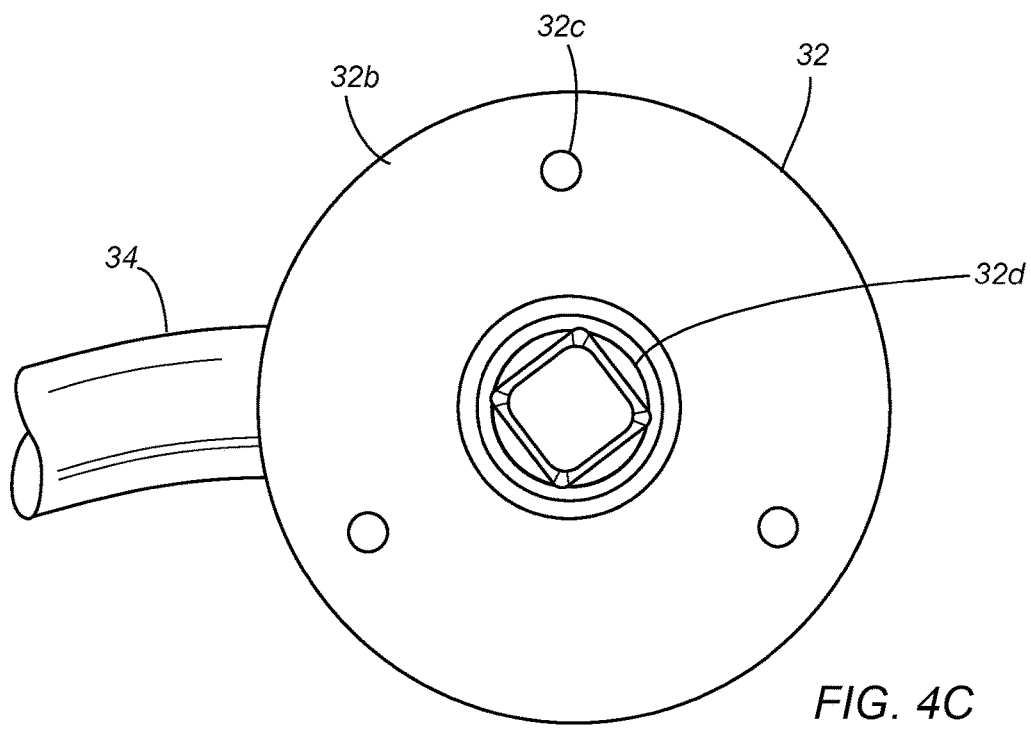

Turning to FIGS. 4A-4C, an exemplary embodiment of a port assembly 30 is shown that includes an injection port 32, an elbow 33 coupled to the injection port 32, a section of tubing 34, and a straight nipple or other connector 35. As best seen in FIGS. 4B and 4C, each injection port 32 may include a mounting plate 32b to which a fitting 32a is attached. In an exemplary embodiment, the injection port 32 may be constructed from metal, plastic, or composite material, e.g., completely of Type 304 stainless steel or food grade plastic, e.g., such that the injection port 32 is completely cleanable, e.g., making it suitable for pharmaceutical applications. The fitting 32a and plate 32b may be formed separately, e.g., by casting, spinning, stamping, machining, molding, and the like, and permanently attached together, e.g., by welding, bonding with adhesive, and the like. In an exemplary embodiment, a threaded fitting 32a may be welded or otherwise coupled to the backside of a flat plate 32b. The weld may be from the front side and is complete, making this a closed weld. Alternatively, the fitting 32a and plate 32b may be integrally formed together, e.g., by casting, machining, molding, and the like.

One or more mounting holes 32c may be provided through the plate 32b, e.g., three holes evenly spaced around an inlet or other opening 32d communicating with the fitting 32a, e.g., by stamping, drilling, machining, and the like. In addition, one or more threads may be provided in the fitting 32a and/or inlet 32d, e.g., to allow other components to be removably coupled to the injection port 32. For example, as best seen in FIG. 4C, a plug 38 may be provided to seal the inlet 32d of the injection port 32, which may be removed, e.g., unthreaded from the injection port 32, at any time to test a filter, e.g., to connect an aerosol generator or other testing system (not shown) to the injection port 32, as described further below.

In an exemplary embodiment, the plate 32b may be formed from sixteen gauge (16 GA) sheet metal having an outer diameter of about three inches (75 mm) and the fitting 32a may have a length between about 1.375-1.5 inches (34-38 mm) tall and have a diameter between about a half inch to one and a half inches (13-39 mm).

The elbow 33 may include a first end 33a configured to be coupled to the fitting 32a of the injection port 32 and a second end 33b configured to be coupled to the tubing 34. For example, the fitting 32a may include internal threads and the first end 33a may including corresponding external threads for threading the elbow 33 into the fitting 32a. Alternatively, other mating connectors may be provided for removably securing the elbow 33 to the fitting 32a, or the elbow 33 may be permanently attached to the fitting 32a, e.g., by welding, bonding with adhesive, and the like. The second end 33b of the elbow 33 may be sized to be inserted into the tubing 34, e.g., including one or more annular barbs or other features for securing the tubing 34 to the elbow 33. The elbow 34 may be formed from metal, e.g., brass, plastic, or composite materials, as desired.

Figure 2:
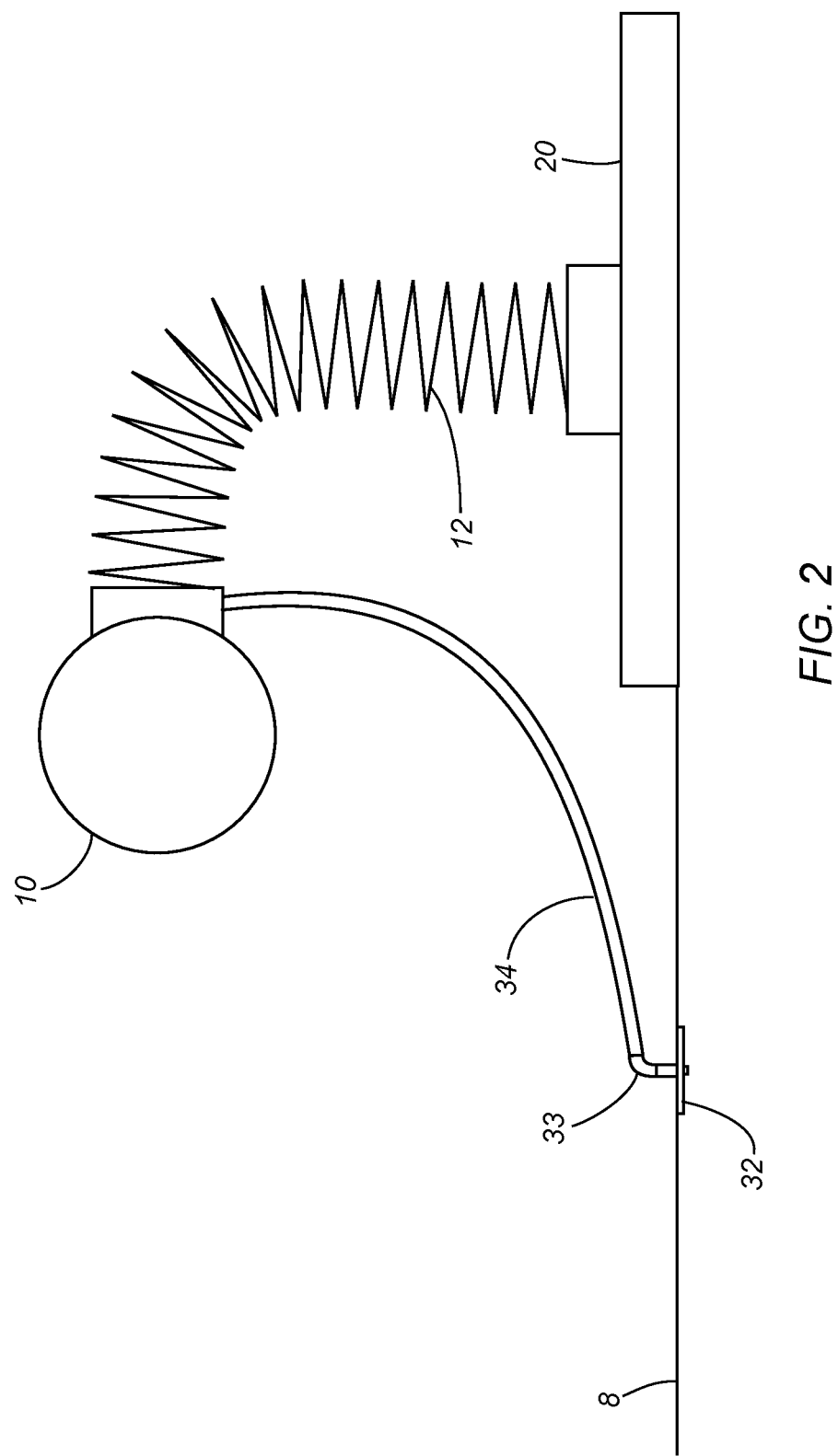
FIG. 2 is a cross-section showing the first branch of the duct system of FIG. 1 including a port assembly having an injection port mounted in a ceiling of the facility and tubing extending from the injection port to the first branch for delivering test materials to the filter from the injection port.

The nipple 35 may include a first end 35a sized to be inserted into the tubing 34, e.g., including one or more annular barbs or other features for securing the tubing 34 to the nipple 35, and a second end 35b configured to be connected to a plate 36 mounted to a duct wall adjacent a filter (such as a wall of the first branch 12 as shown in FIG. 2). In an exemplary embodiment, the plate 36 may include a threaded fitting 36a, and the second end 35b of the nipple 35 may be threaded into the fitting 36a. The nipple 35 may be formed similar to the elbow 33, e.g., from metal, e.g., brass, plastic, or composite materials, by casting, machining, molding, and the like. Optionally, the nipple 35 may be replaced with an elbow similar to the elbow 33, if a bend is needed at the terminal end of the tubing 34.

The tubing 34 may be formed from flexible plastic material, e.g., PEX, and the like, that may be routed as desired from the port 32 to a duct branch or filter. The tubing 34 may be provided in set lengths or a relatively long length of tubing may be provided that may be cut to length as desired, e.g., when the distance from the mounting location of the injection port 32 to the plate 36 and/or installation route are known.

The port assembly 30 may be provided as a kit, e.g., including the injection port 32, elbow 33, nipple 35, plug 38, and optionally tubing 34 as separate components that may be assembled at a facility, e.g., when the duct system 10 and filters 20 are initially installed, or may be added to an existing system. For example, a facility may include multiple filters at different locations and a port assembly 30 may be provided for each filter. During use, the injection port(s) 32 may be mounted at one or more locations that are easily accessible, while the other components are installed between the access location and the respective filter 20, e.g., within the attic space of the facility where they may remain indefinitely.

Figure 6:
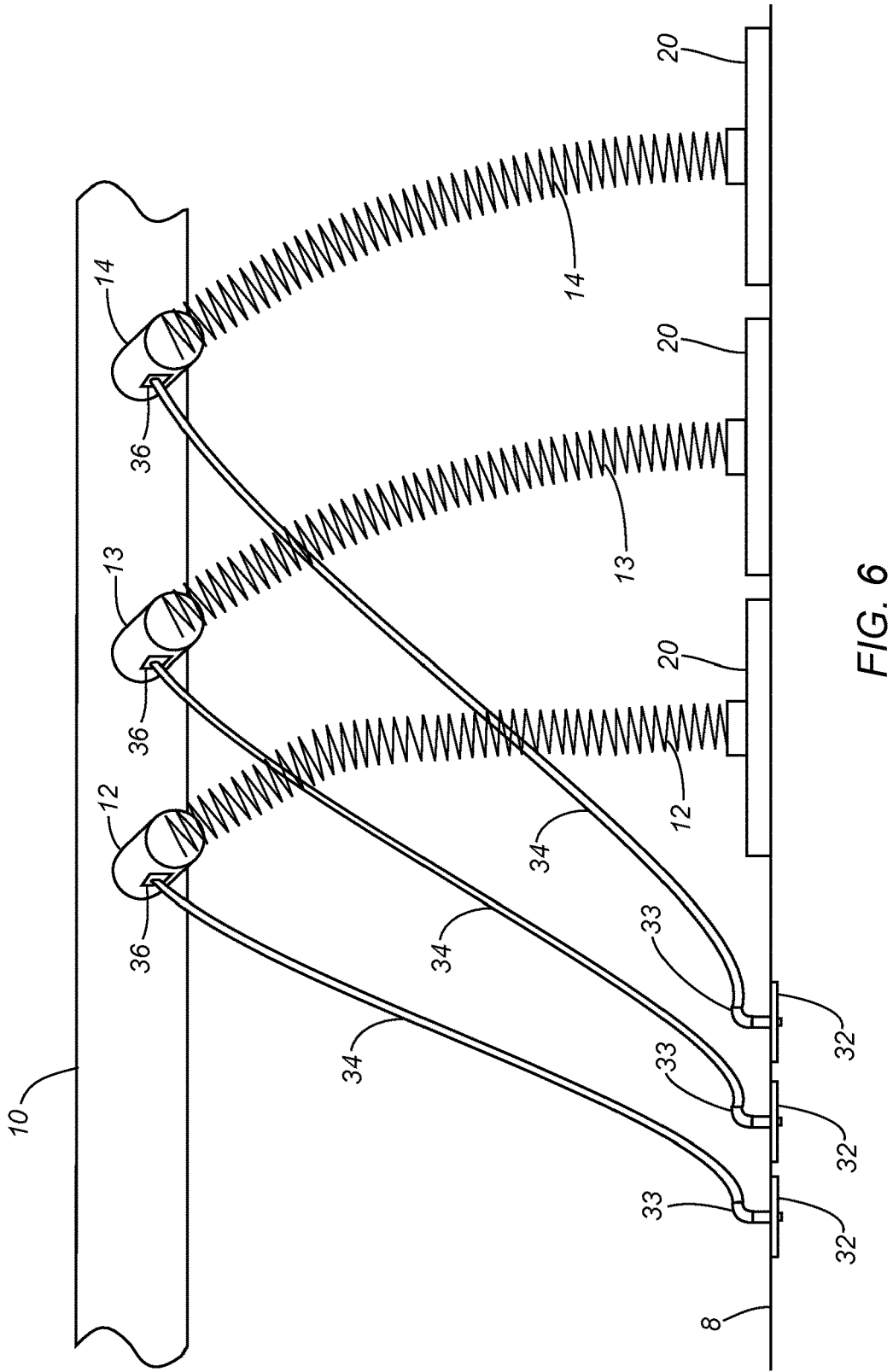
FIG. 6 is a cross-section view of a portion of a duct system of a facility including multiple branches communicating with respective filters, and including port assemblies for delivering test materials to the filters from a location remote from the duct system.

For example, with reference to the exemplary duct system 10 shown in FIGS. 1 and 2, two port assemblies 30 are shown for delivering aerosol or other test materials to respective filters 20 in the first and second branches 12, 14 of the system 10. During installation, the injection ports 32 are mounted to the ceiling 8 of the facility at a desired location. As shown in FIGS. 3A, 3B, and 6, in an exemplary installation, multiple injection ports 32 may be mounted adjacent one another at a desired access location in the ceiling 8, thereby allowing each of the desired filters to be tested without moving the testing system to be moved to multiple locations within the facility.

In an exemplary installation, holes are drilled, cut, or otherwise formed in the ceiling 8 and the fitting 32a of each injection port 32 is inserted into a respective hole. Fasteners 40 (e.g., bolts, screws, and the like) are directed into the holes 32c of the plate 32b (not shown, see, e.g., FIG. 4C) to secure the injection ports 32 to the ceiling 8, e.g., as shown in FIG. 3A, and/or isolate the region above the ceiling 8 from the room once installation is complete. An elbow 33 may be threaded into (or otherwise connected to) the fitting 32a above the ceiling, e.g., as shown in FIG. 3B, and tubing 34 may be connected to the elbow 33 (not shown).

Figure 5:
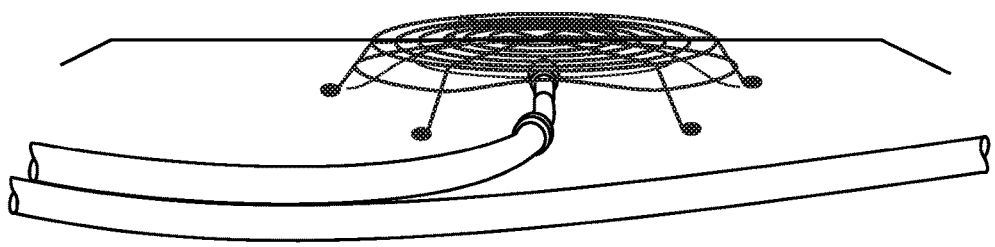
FIG. 5 shows an alternative embodiment of a port assembly for delivering test material directly to a non-ducted filter.

In addition, a plate 36 may be mounted into the wall of each branch 12, 14 immediately adjacent the respective filter 20. For example, an opening may be cut into the wall of the first branch 12, and one or more fasteners (e.g., bolts, screws, and the like) may be directed through holes of the plate 36 into the wall to secure the plate 36 to the wall of the first branch 12. If the duct of the first branch 12 includes external insulation, the insulation may be removed as necessary to expose the wall of the duct and allow the plate 36 to be mounted thereto. Alternatively, a plate or other connector may be provided directly on the filter 20 or the tubing 34 may be inserted into an opening into the interior of the duct. In a further alternative, shown in FIG. 5, the port assembly 30 may be used for testing non-ducted filters, e.g., by directing the tubing 34 to the intake of a blower of a fan-powered filter. Optionally, the tubing 34 and/or nipple 35 may be secured relative to the intake of the blower to prevent migration of the tubing 34.

With multiple port assemblies installed, any of the associated filters may be tested at any time, as desired. For example, in the configuration shown in FIGS. 3A and 3B, seven port assemblies 30 are provided that communicate with separate filters, allowing any or all of the filters to be tested. When the injection ports 32 are installed, each may be labeled to identify the filter they service, e.g., one for each filter in the system, thereby facilitating subsequent testing.

For example, during a test of the filter 20 communicating with the first branch 12 in FIGS. 1 and 2, a plug 38 (not shown, see, e.g., FIGS. 4A-4C) may be removed to allow access to the inlet 32d of the injection port 32. A nipple or other test line 42 may be coupled to the inlet 32d. e.g., threaded into the injection port 32, as shown in FIG. 3A. An aerosol generator or other testing system (not shown) may be coupled to the test line 42, and activated (e.g., by turning on an air compressor, not shown, of the testing system), whereupon aerosol (smoke) and/or other test media may be delivered into the injection port 32, through the elbow 33 and tubing 34 into the first branch 12 to test the filter 20 without exposing other sections of the system 10, such as second branch 14 to the media. The filter 20 may be scanned using conventional methods, e.g., using an aerosol photometer to assess whether the filter 20 is functioning properly.

Upon completion of the test, the testing system may be deactivated, the test line 42 disconnected from the injection port 32, and the plug 38 replaced into the inlet 32d. This process may be repeated for each of the desired injection ports 32 and filters within a facility.

It will be appreciated that the injection port 32 of a port assembly 30 may be installed just about anywhere in a facility. For a typical installation, a cleanroom may have an adjacent gown or ante room, and one or more injection ports may be mounted in the ceiling of the ante room or outside of the area completely. The tubing may be routed from the port(s) to the duct line that feeds each individual filter (or directly to the inlet of the filter or its blower, e.g., for non-ducted applications). Thus, the testing equipment may remain outside the cleanroom in the ante room, yet used to access and test each filter, as desired.

The systems and methods herein may provide one or more of the following benefits. For example, the systems may:
1. require one time only installation (while allowing testing any time after installation as desired);
2. may make it possible to test filters that are not able to be tested using conventional methods;
3. may streamline certification activities;
4. may eliminate the need to access the area above the ceiling within the clean space of a facility;
5. may provide infection control since no access above the ceiling means no worries with undesired exposures;
6. may eliminate the need to cut out caulked-in ceiling tiles during each service;
7. may eliminate exposure of non-filtered air into the clean space;
8. may keep 99% of the test equipment either in the ante room or completely outside of the facility all together;
9. may minimize quantity of aerosol used during testing by only feeding the filter being tested and not all the filters at once;
10. may minimize facility down time by up to 90%.
11. may reduce certification time in half, leading to substantial annual savings;
12. may allow a facility to choose where the ports are installed to create an owner-controlled testing plan;
13. may make it possible for facilities to be compliant with the relevant standards by providing a method to properly challenge the HEPA filters. The benefits are extensive and the installations are applicable to an endless number of facilities worldwide.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A method for installing a testing system for delivering test media into a duct system of a facility to test a filter of the duct system, comprising:
   mounting an injection port to a wall or a ceiling of an accessible location within the facility;
   coupling a first end of a section of tubing to the injection port;
   mounting a delivery port to a wall of a duct branch delivering air to the filter; and
   coupling a second end of the section of the tubing to the delivery port, thereby creating a path for test media from the accessible location to the filter via the duct branch without exposing other sections of the duct system to the test media.

2. The method of claim 1, wherein the injection port is mounted to a ceiling of the facility.

3. The method of claim 1, wherein mounting the injection port comprises:
   cutting an opening in a ceiling of the facility;
   inserting a fitting of the injection port through the opening until a plate of the injection port contacts the ceiling; and
   securing the plate to the ceiling.

4. The method of claim 3, further comprising coupling an elbow to the fitting above the ceiling, and wherein coupling a first end of a section of tubing to the injection port comprises coupling the first end of the section of tubing to the elbow.

5. The method of claim 1, further comprising inserting a plug into the injection port.

6. The method of claim 1, wherein the filter is located within a cleanroom and wherein the injection port is mounted in a ceiling outside the cleanroom.

7. The method of claim 6, wherein the injection port is mounted in a ceiling of an anteroom adjacent the cleanroom.

8. The method of claim 1, wherein the injection port is a first injection port, the delivery port is a first delivery port, and the section of tubing is a first section of tubing, the method further comprising:
   mounting a second injection port to a wall or a ceiling of a second accessible location within the facility;
   coupling a first end of a second section of tubing to the second injection port;
   mounting a second delivery port to a wall of a second duct branch delivering air to a second filter; and
   coupling a second end of the second section of tubing to the second delivery port, thereby creating a path for test media from the second accessible location to the second filter via the second duct branch without exposing other sections of the duct system to the test media.

9. The method of claim 1, wherein mounting the delivery port comprises directing one or more fasteners through a plate of the delivery port into the wall of the duct branch, and wherein the second end of the section of the tubing is coupled to a fitting extending from the plate.

10. The method of claim 9, further comprising removing external insulation from the first branch to expose the wall of the duct branch before mounting the delivery port.

11. The method of claim 1, wherein the delivery port is mounted to the wall of the duct branch in an attic space external to the filter.

12. A method for installing a testing system for delivering test media into a duct system of a facility to test filters of a duct system of a facility including a plurality of branches communicating with respective filters, comprising:
   mounting a plurality of injection ports to a wall or ceiling of an accessible location within the facility;
   coupling a first end of respective sections of flexible tubing to each injection port;
   mounting a delivery port to a wall of a branch of the duct system delivering air to each filter; and
   coupling a second end of the respective sections of the tubing to respective delivery ports, thereby creating separate paths for test media from respective injection ports at the accessible location to respective filters without exposing other sections of the duct system to the test media other than the branches corresponding to the respective filters.

13. The method of claim 12, wherein the filters are located within a cleanroom and wherein the injection ports are mounted in a ceiling outside the cleanroom.

14. The method of claim 13, wherein the injection ports are mounted in a ceiling of an anteroom adjacent the cleanroom.

15. The method of claim 13, wherein each delivery port is mounted to a branch of the duct system in an attic space of the facility outside the cleanroom.

16. The method of claim 12, further comprising labeling each of the injection ports to identify the filter they service, thereby facilitating subsequent testing.

17. A kit for installing a testing system for delivering aerosol into a duct system of a facility to test a filter of a duct system of a facility, comprising:
   a section of tubing formed from flexible plastic material;
   an injection port including a mounting plate and a fitting extending from the mounting plate;
   an elbow comprising a first end configured to be coupled to the fitting and a second end including one or more elbow connectors for connecting the elbow to a first end of the section of tubing;
   a delivery port including a plate configured to be mounted to a wall of a duct branch and a fitting; and
   a nipple comprising a first end configured to be coupled to the fitting of the delivery port and a second end including one or more nipple connectors for connecting the nipple to a second end of the section of tubing to create a path for test media from the injection port to the duct branch without exposing other sections of the duct system to the test media.

18. The kit of claim 17, wherein the first end of the elbow and the fitting include mating threaded connectors.

19. The kit of claim 17, wherein the first end of the nipple and the fitting of the delivery port fitting include mating threaded connectors.

20. The kit of claim 17, further comprising a plug for closing an inlet in the injection port mounting plate.

21. The kit of claim 17, wherein the injection port is a first injection port, the elbow is a first elbow, and the nipple is a first nipple, the kit further comprising:
   a second injection port including a second mounting plate and a second fitting extending from the second mounting plate;
   a second elbow comprising a first end configured to be coupled to the second fitting of the second injection port and a second end including one or more barb connectors for connecting to a first end of a second section of tubing;
   a second delivery port including a second plate configured to be mounted to a wall of a second duct branch and a second fitting; and
   a second nipple comprising a first end configured to be coupled to the second fitting of the second delivery port and a second end including one or more barb connectors for connecting to a second end of a second section of tubing to create a second path for test media from the second injection port to the second duct branch without exposing other sections of the duct system to the test media.

22. The kit of claim 17, wherein the plate of the delivery port is flat and includes one or more holes to receiving fasteners to mount the plate to a wall of a duct branch.

23. The kit of claim 17, wherein the fittings and the section of tubing have a diameter between about a half inch to one and a half inches.

* * * * *